United States Patent
Xia et al.

(10) Patent No.: US 10,168,371 B2
(45) Date of Patent: Jan. 1, 2019

(54) SYSTEM AND METHODS FOR DETERMINING THE IMPACT OF MOISTURE ON DIELECTRIC SEALING MATERIAL OF DOWNHOLE ELECTRICAL FEEDTHROUGH PACKAGES

(71) Applicant: Pacific Aerospace & Electronics, Inc., Wenatchee, WA (US)

(72) Inventors: Hua Xia, Huffman, TX (US); Tucker Havekost, Leavenworth, WA (US); Daniel Brown, Wenatchee, WA (US); Erich Preissler, Wenatchee, WA (US); Mike Grimm, Wenatchee, WA (US)

(73) Assignee: PA&E, HERMETIC SOLUTIONS GROUP, LLC, Wenatchee, WA (US)

( * ) Notice: Subject to any disclaimer, the term of this patent is extended or adjusted under 35 U.S.C. 154(b) by 107 days.

(21) Appl. No.: 15/478,293

(22) Filed: Apr. 4, 2017

(65) Prior Publication Data
US 2018/0284176 A1 Oct. 4, 2018

(51) Int. Cl.
| | |
|---|---|
| *H01B 1/00* | (2006.01) |
| *G01R 31/00* | (2006.01) |
| *G01R 31/16* | (2006.01) |
| *G01R 31/20* | (2006.01) |
| *G01R 31/12* | (2006.01) |
| *H01G 2/00* | (2006.01) |
| *C12Q 1/00* | (2006.01) |

(52) U.S. Cl.
CPC ....... *G01R 31/003* (2013.01); *G01R 31/1263* (2013.01); *G01R 31/16* (2013.01); *G01R 31/20* (2013.01); *C12Q 1/00* (2013.01); *H01B 1/00* (2013.01); *H01G 2/00* (2013.01)

(58) Field of Classification Search
CPC ............... H01B 1/00; H01G 2/00; C12Q 1/00
See application file for complete search history.

(56) References Cited

U.S. PATENT DOCUMENTS

| | | | |
|---|---|---|---|
| 5,017,740 | A | 5/1991 | Honkomp et al. |
| 6,957,981 | B2 | 10/2005 | Karino et al. |
| 7,168,984 | B2 | 1/2007 | Perle et al. |
| 7,364,451 | B2 | 4/2008 | Ring et al. |

(Continued)

*Primary Examiner* — Jermele M Hollington
*Assistant Examiner* — Temilade Rhodes-Vivour
(74) *Attorney, Agent, or Firm* — PatentFile, LLC; Bradley C. Fach; Steven R. Kick

(57) ABSTRACT

A system for determining the impact of moisture on a dielectric sealing material may include a testing apparatus having a testing chamber. A dielectric sealing material and a conducting pin may be exposed to the testing chamber. A first electrical lead may be coupled to the conducting pin, and a second electrical lead may be coupled to the dialectic material. An insulation resistance measurement unit may be coupled to both the first electrical lead and the second electrical lead, and the insulation resistance measurement unit may be configured to measure an insulation resistance value between the electrical leads. The insulation resistance measurement unit may measure a first insulation resistance value of the dielectric sealing material in a first environmental condition, and the insulation resistance measurement unit may measure a second insulation resistance value of the dielectric sealing material at a second environmental condition, that is different than the first environmental condition.

20 Claims, 11 Drawing Sheets

(56) References Cited

U.S. PATENT DOCUMENTS

| | | |
|---|---|---|
| 7,901,247 B2 | 3/2011 | Ring |
| 8,082,663 B1 | 12/2011 | Monroe et al. |
| 9,553,398 B2 | 1/2017 | True et al. |
| 2005/0136500 A1* | 6/2005 | Yang ................. G01N 33/52 435/14 |
| 2010/0210745 A1* | 8/2010 | McDaniel .............. C09D 5/008 521/55 |
| 2012/0018216 A1* | 1/2012 | Harada ................ H01B 17/305 174/650 |
| 2013/0189865 A1* | 7/2013 | Zaiser ................... H01R 13/52 439/190 |
| 2014/0168850 A1* | 6/2014 | Stevenson ............ A61N 1/3718 361/302 |

* cited by examiner

SYSTEM AND METHODS FOR DETERMINING THE IMPACT OF MOISTURE ON DIELECTRIC SEALING MATERIAL OF DOWNHOLE ELECTRICAL FEEDTHROUGH PACKAGES

FIELD OF THE INVENTION

This patent specification relates to the field of identifying and testing of electrical feedthrough package sealing materials used for downhole logging tools. More specifically, this patent specification relates to the field of identifying and testing of electrical insulation performance of a high-pressure and high-temperature electrical feedthrough package under simulated moisture-rich downhole conditions.

BACKGROUND

Electrical feedthroughs used in downhole logging tools, logging while drilling (LWD), and measurement while drilling (MWD) tools, as well as any other electronic instruments capable of being used in a downhole environment, are subjected to a variety of harsh operating environments. These electrical feedthroughs may carry substantial amounts of power with electrical signals which may be of a few thousand volts and/or of a few hundred ampere electric currents. The electronic instruments within a downhole logging tool requires a hermetic type electrical feedthrough that is able to interconnect with surface instruments for providing power, control signal, data transmission, and the like. The electrical feedthroughs must survive in extreme hostile liquid environments, such as brine, oil and water base drilling mud, and fluids that may contain hydrogen sulfide, carbon dioxide, methane, and moisture, including pressures of up around 30,000 PSI and temperatures of ~177 degrees Celsius which are commonly encountered in downhole environments.

Usually, downhole logging instruments known as logging sondes are lowered into boreholes to make, for example, formation evaluation measurements, and infer properties of the formation surrounding the borehole and the fluids (gas, oil, water, or a mixed multi-phase) in the formation. These downhole logging tools may be an acoustic/ultrasonic logging tool, a neutron or gamma-ray density tool, a formation identification tool for measuring the earth formations surrounding a borehole, such as in a hydrocarbon (e.g., oil, natural gas, etc.) well. Such downhole logging instruments may be used to make such measurements while the well is being drilled, which is referred to as logging-while-drilling (LWD) or measurement-while-drilling (MWD). The LWD or MWD techniques may allow corrective actions to be taken during the drilling processes if desired. For example, borehole information, if available, in real time may be used to make adjustments to mud weights to prevent formation damage and to improve well stability. In addition, real time formation log data may be used to direct a drill bit in the desired direction. Usually, a downhole logging tool has electrical conductors mounted on the tool housing in a tubular structure. The logging tool includes a metal housing and an electrical wireline. A bulkhead is coupled to a tool housing that includes a metal shell for protecting an electrical connecting pins assembly. The electrical connecting pin is coupled to the exterior wireline cable, and to the interior electronic circuits, and a dielectric sealing material is used to insulate the electrical transmissions from logging tool electronics to the wireline cable to surface power or data processing unit. The downhole logging tool may be required for an open-hole or a closed-hole service bypassing a wellhead. A wireline cable not only mechanically supports the downhole tool but also simultaneously provides electrical power to the tool and sends the measured data back to a surface data process unit. A wellbore may be filled with fluids that may contain certain amounts of water and moisture. The electronics inside the downhole tool housing require a hermetic type electrical feedthrough (singular or multi-pin) that interconnects with surface power or data processing unit for power and control of the signal transmissions, or for data transmissions. For a plurality of logging sondes based downhole tools, each individual logging sonde has at least two electrical feedthroughs as interconnects for power or control signal transmissions. The extremely harsh environment deployable electrical feedthrough package should not only survive the elevated downhole temperatures at 30,000 PSI pressure but also require high corrosion-resistance for ensuring long-term operation reliability.

A hermetically sealed electrical feedthrough package could protect the inside of logging or measurement electronics or instruments from extreme hostile liquid environments, however, the electrical resistivity of the dielectric sealing material may be not only be rapidly declined with elevated downhole temperature but also decreased when exposed to water or moisture, thereby potentially causing catastrophic downhole tool electric failures either by dielectric sealing material moisture absorption or by its hydrophilicity.

Therefore a need exists for novel systems and methods for determining the impact of moisture on dielectric sealing material of an electrical feedthrough package. There is also a need for an evaluation system and method to identify if an electrical feedthrough package has high moisture resistance under simulated downhole conditions. A further need exists, for an evaluation system and method to identify if the dielectric sealing material of a downhole electrical feedthrough package has high moisture resistance or hydrophobicity under water-based or moisture-rich oil-based wellbores. More specifically, a need exists for an evaluation system and method for measuring electrical insulation resistance of an electrical feedthrough in general, and moisture resistance from the downhole electrical feedthrough package in particular, for enabling downhole logging tools, LWD and MWD tools to have reliable operation in water-based or moisture-rich oil-based wellbores.

BRIEF SUMMARY OF THE INVENTION

According to one aspect consistent with the principles of the invention, a system for determining the impact of moisture on dielectric sealing material of a downhole electrical feedthrough package is provided. In some embodiments, the system may include a testing apparatus having a testing chamber preferably surrounded by a rigid shell. A dielectric sealing material and a conducting pin may be positioned within the rigid shell and exposed to the testing chamber. A first electrical lead may be coupled to the conducting pin, and a second electrical lead may be coupled to the dialectic material. An insulation resistance measurement unit may be coupled to both the first electrical lead and the second electrical lead, and the insulation resistance measurement unit may be configured to measure an insulation resistance value between the electrical leads. A fluid conducting aperture may be positioned within the rigid shell, and the fluid conducting aperture may be configured to transfer a hydraulic pressurized fluid into the testing chamber. The insulation resistance measurement unit may measure a first insulation resistance value of the dielectric sealing material in a first environmental condition, and the insulation resistance measurement unit may measure a second insulation resistance value of the dielectric sealing material at a second environmental condition, that is different than the first environmental condition, after a hydraulic pressurized fluid, such as water or oil, has been introduced into the testing chamber for a period of testing time.

According to another aspect consistent with the principles of the invention, a testing apparatus for determining the impact of moisture on dielectric sealing material's performance is provided. In some embodiments, the apparatus may include a testing chamber, configured to secure a dielectric sealing material surrounded by a rigid shell. A dielectric sealing material may be positioned within the testing chamber, and the dielectric sealing material may surround all or a portion of a conducting pin. A first electrical lead may be electrically coupled to the conducting pin, and a second electrical lead may be electrically coupled to the dialectic material preferably by being coupled to metal shell or to a plate that is coupled to the dielectric sealing material. An insulation resistance measurement unit may be coupled to both the first electrical lead and the second electrical lead, and the insulation resistance measurement unit configured to measure an insulation resistance value between the electrical leads.

According to yet aspect consistent with the principles of the invention, a method for determining the impact of moisture of a dielectric sealing material is provided. In some embodiments, the method may include the steps of: measuring a first insulation resistance value between a dielectric sealing material and an electrically conductive pin at a first temperature, a first hydraulic pressure, and a first moisture content; increasing the temperature of the testing chamber to a second temperature; introducing a hydraulic pressurized fluid to the dielectric sealing material to create a second moisture content; and measuring a second insulation resistance value between the dielectric sealing material and the electrically conductive pin and storing the second insulation resistance value in the data logging unit.

According to still a further aspect consistent with the principles of the invention, in some embodiments, a high moisture-resistant dielectric sealing material may be characterized by a power response function of $R(t)=R_o \cdot t^v$, while moisture sensitive dielectric sealing material may be characterized by a negative exponential function of $R(t)=R_o \cdot \exp(-at)$.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Figure 1:
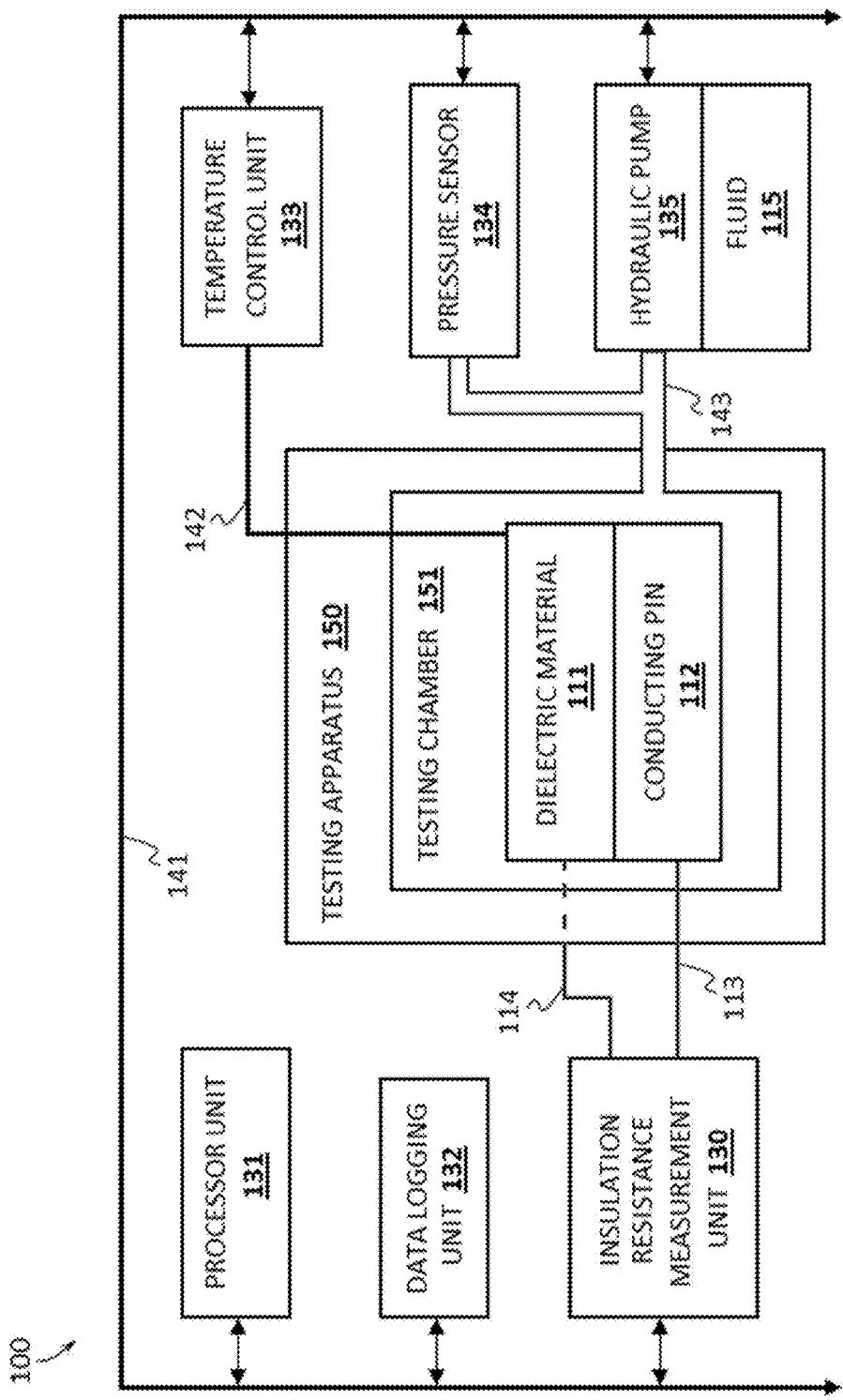
FIG. 1 depicts a schematic diagram of an example of a system for determining the impact of moisture on dielectric sealing materials according to various embodiments described herein.

For purposes of description herein, the terms "upper", "lower", "left", "right", "rear", "front", "side", "vertical", "horizontal", and derivatives thereof shall relate to the invention as oriented in FIG. 1. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Although the terms "first", "second", etc. are used herein to describe various elements, these elements should not be limited by these terms. These terms are only used to distinguish one element from another element. For example, the first element may be designated as the second element, and the second element may be likewise designated as the first element without departing from the scope of the invention.

As used in this application, the term "about" or "approximately" refers to a range of values within plus or minus 10% of the specified number. Additionally, as used in this application, the term "substantially" means that the actual value is within about 10% of the actual desired value, particularly within about 5% of the actual desired value and especially within about 1% of the actual desired value of any variable, element or limit set forth herein.

A new system and methods for determining the impact of moisture on dielectric sealing materials are discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

The present invention will now be described by example and through referencing the appended figures representing preferred and alternative embodiments. FIG. 1 illustrates an example of a system for determining the impact of moisture on dielectric sealing materials ("the system") 100 according to various embodiments. In this example and in some embodiments, the system 100 may comprise a testing apparatus ("the apparatus") 150 having a testing chamber 151 with a dielectric sealing material 111 and a conducting pin 112 positioned within the testing apparatus 150 and exposed to the testing chamber 151. A first electrical lead 113 may be coupled to the conducting pin 112, and a second electrical lead 114 may preferably be coupled to the testing apparatus 150, with the dialectic sealing material 111 positioned between the first electrical lead 113 and the second electrical lead 114. An insulation resistance measurement unit 130 may be coupled to both the first electrical lead 113 and the second electrical lead 114. The insulation resistance measurement unit 130 may be configured to measure an insulation resistance value between the electrical leads 113, 114.

The apparatus 150 may comprise a fluid conducting aperture 152 which may be configured to transfer a hydraulic pressurized fluid 115 into the testing chamber 151. The insulation resistance measurement unit 130 may measure a first insulation resistance value of the dielectric sealing material 111 in a first environmental condition, and the insulation resistance measurement unit 130 may measure a second insulation resistance value of the dielectric sealing material 111 at a second environmental condition after the hydraulic pressurized fluid 115 has been introduced into the testing chamber 151 for a period of time. A second environmental condition is different that a first environmental condition. A second environmental condition may comprise a second temperature, a second pressure, and/or a second moisture content that may be different than a first temperature, a first pressure, and a first moisture content of a first environmental condition. The difference between the insulation resistance values of the dielectric sealing material 111 measured while the dielectric sealing material is subjected to a first environmental condition and measured while the dielectric sealing material is subjected to a second environmental condition may be used to determine moisture resistance of the dielectric sealing material 111. In some embodiments, a second environmental condition may have a second temperature that is greater than 177 degrees Celsius and a second pressure that is greater than 10,000 PSI. In preferred embodiments, a second environmental condition may have a second temperature that is 20 to 300 degrees Celsius greater than a first temperature of a first environmental condition and/or a second pressure that is 10,000 to 35,000 PSI greater than a first pressure of a first environmental condition.

In some embodiments, the system 100 may comprise an insulation resistance measurement unit 130. An insulation resistance measurement unit 130 may comprise an ohmmeter suitable for measuring the electrical resistance of insulators such as a dielectric sealing material 111. In preferred embodiments, an insulation resistance measurement unit 130 may comprise a Megohmmeter (sometimes referred to as a megger) which can provide high DC voltages (typically in ranges from 500 DCV to 2.5 k DCV) at specified current capacity.

A dielectric sealing material 111 may comprise an electrically insulating material, such as polymer, glass, glass-ceramic, or ceramic materials, which are desired to be tested under simulated downhole harsh environmental conditions. A conducting pin 112 may comprise an electrically conducting material, such as copper, copper-alloy, Inconel alloy, Kovar, Alloy52, and Titanium etc., which may be used to form electrical connections between a downhole wireline tool and a wireline cable. For a dielectric sealing material 111 to be a suitable candidate for use as an electrical insulator around these electrical connections, the dielectric sealing material 111 must have high electrical insulation resistance and long-time reliability, even deployed in water-based or moisture-rich downhole conditions which may be simulated in the apparatus 150 by the system 100.

To make hermetically sealed electrical feedthroughs, a highly insulating dielectric material, such as a glass, glass-ceramic or ceramic, is used to seal electric conducting pin(s) in a metal enclosure of a multi-pin electrical feedthrough. At a firing temperature, close to softening point of the sealing material, the glass hollow cylinder will bound both conducting pin and metal shell together after cooling to ambient. The hermeticity of $\sim 1 \times 10^{-9}$ cc/sec (He at 1 atm differential) is normally checked with a leak detection instrument. On the other hand, the insulation strength is also normally checked with an insulation resistance measurement unit 130, such as a Megohmmeter, where the required minimum insulation resistance has to be met at a specific testing voltage, for example, 2 MΩ, at 600-1000 DCV for most of electrical equipment, recommended by International Electrical Testing Association (NETA).

Figure 7:
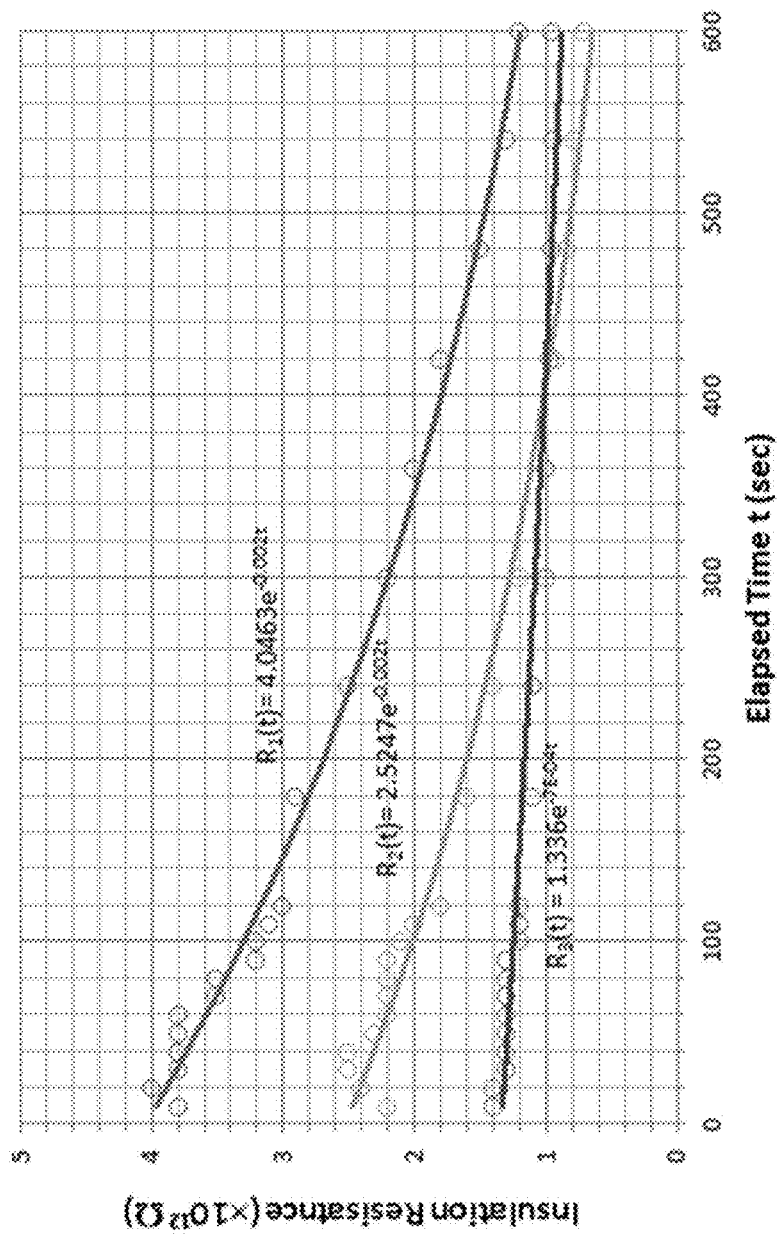
FIG. 7 depicts a graph showing typical effective insulation resistance measurements from three example moisture-sensitive dielectric sealing material sealed based electrical feedthrough packages subsequent to boiling in water for 1-2 hours duration.

However, the minimum required insulation resistance is different when using a testing voltage from 250V to 15,000V. In fact that the electrical conductivity of the dielectric sealing material may not only rapidly rise at downhole temperature but also possible increase when exposes to water-based or moisture-rich fluids. The degradation of the insulation resistance is more related to hydrophilic property of the dielectric sealing material. On the other hand, the loss of the insulation resistance is simply because the moisture $OH^{-1}$ hydroxyl ions contained fluid may physically condensed onto the sealing material surface or may be absorbed by the dielectric sealing material. The system 100 enables identifying if a dielectric sealing material sealed electrical feedthrough can be deployed in water-based or moisture-rich oil wellbores. To measuring moisture resistance from a dielectric sealing material, FIG. 7 provides exemplary effective insulation resistance measurements from three dielectric sealing material based electrical feedthrough packages, subsequent to boiling in water for 1-2 hours duration. Initial dry ambient insulation resistance from each sample dielectric sealing material has first been measured at 500 DCV with the value from 10 TΩ to a few hundred TΩ (or 1 TΩ=1×10$^{12}$Ω). The measured insulation resistance (IR) values from three feedthroughs have shown a negative exponential function of time. Such a time-decayed IR values strongly indicates unacceptable insulation strength, especially, the measured dielectric absorption ratio, IR (60)/IR (30) is less than 1.0, implying the dielectric sealing material may have a layer of high conductive surface, as explained below.

For a water insoluble dielectric sealing material its electrical insulation resistance should be determined only by its volumetric resistivity (ρ) and feedthrough geometries, which is described by $$R_v = \frac{\rho\left(\frac{\phi_g}{\phi_p} - 1\right)}{2\pi L}, \quad (1)$$

where ρ is resistivity in Ω-cm, L is sealing length, $\phi_g$ and $\phi_p$ are outer and inner diameter of the sealing glass hollow cylinder, respectively. Obviously, the higher the resistivity is, the higher the insulation resistance is for a dielectric sealing material. On the other hand, the shorter sealing length and larger ratio of the outer and inner diameter of the glass hollow cylinder are, the higher the insulation resistance is for an electrical feedthrough package. The desired resistivity should be in order of 1.0×10$^{14}$ Ω·cm, corresponding to a specific sealing length of L=6.3 mm and the ratio of $\phi_g/\phi_p \approx 2.5$.

Since the water boiling process is under atmospheric pressure, it is more likely that the surface of the dielectric sealing material has become conductive due to $OH^{-1}$ hydroxyl ion contained fluid by dipole interaction with poled material surface. If assuming a surface layer has a thickness of $h_s$ with surface resistance of $R_s$, the effective insulation resistance could be approximately written as $$R = \frac{R_v \cdot R_s}{f_1 R_v + f_2 R_s}, \quad (2)$$

Where $R_v$ is volumetric resistance. $f_1$ ($f_2$) is fraction of the surface layer (S) thickness over total sealing length, and $f_1+f_2=1$. It is clear that R could be equal to $R_v$ if $R_s \sim \infty$, which corresponds to perfectly clean and insulating surface. On the other case, R<<$R_v$ if $R_s \to 0$, for a highly hydrophilic sealing material surface that may has a layer of condensed conductive ion contained fluid. However, if this thin layer of the moisture rich surface may have a surface resistance Rs neither infinity nor zero but a function of time approaching infinity because of moisture evaporation process under downhole temperature, the measured insulation resistance may depends upon how fast the moisture molecules are outer diffused from the sealing material surface. In another case, if there is a balance between condensed conductive fluid and evaporated outer fluid, the measured insulation resistance may be lower than ambient insulation resistance values by a constant offset. In further case, the trend of the conductive ion-based fluid accumulated more than the evaporated quantity, the electrical insulation could be degraded as function of time until it eventually causes electrical breakdown of an electrical feedthrough.

Figure 8:
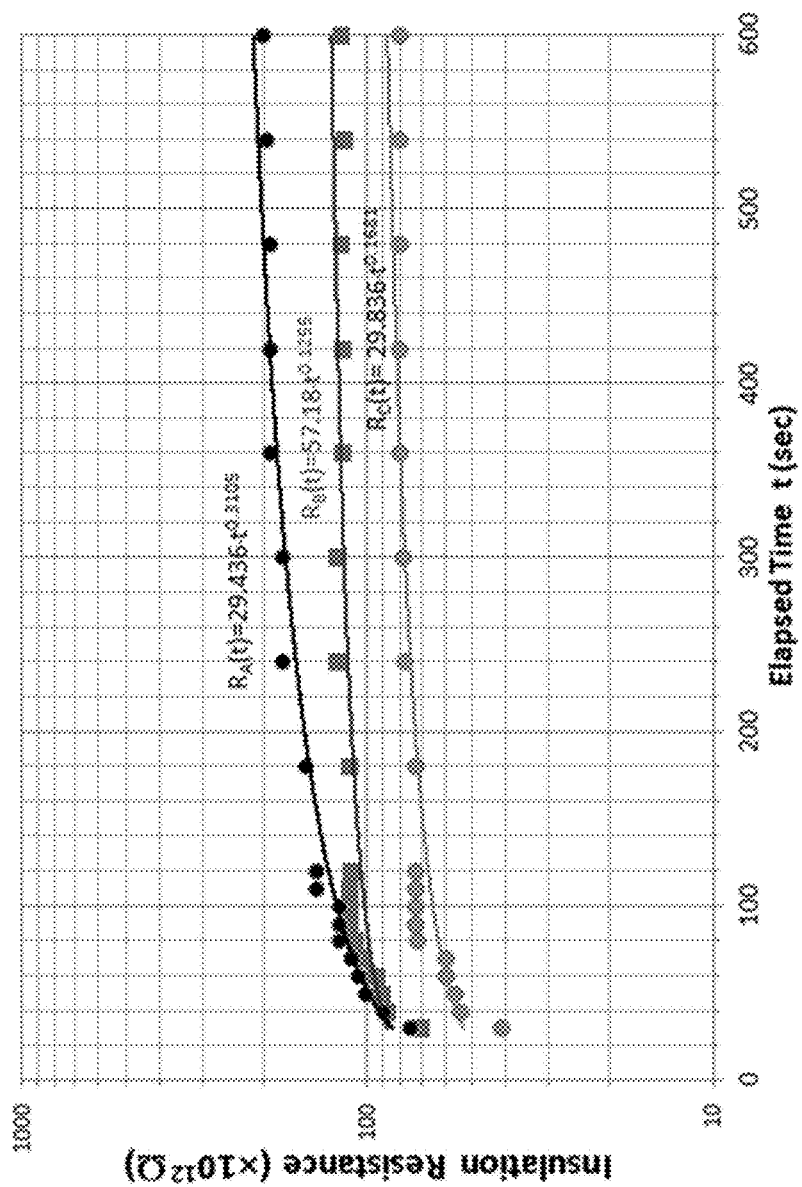
FIG. 8 illustrates a graph showing measured effective insulation resistance values from three example moisture-resistant dielectric sealing material sealed electrical feedthrough packages subsequent to boiling in water for 1-2 hours duration.

FIG. 8 illustrates a graph showing measured effective insulation resistance values from three example dielectric sealing material sealed electrical feedthrough packages subsequent to boiling in water for 1-2 hours duration. Initial dry ambient insulation resistance from each sample has first been measured at 500 DCV with the value normally from 10 TΩ to a few hundred TO. Before to measure boiling water soaking treated feedthrough prototypes the surface water fluid has to be puffed out to avoid electric arc, the measured insulation resistance (IR) values from three electrical feedthrough prototypes have shown that the IR value is a power function of time, namely, $R(t)=R_o \cdot t^v$ (v is constant), and the measured dielectric absorption ratio, IR(60)/IR(30) is (1.40±0.05), implying the dielectric sealing material has acceptable insulation strength or has desirable moisture resistant properties after ambient boiling water soaking treated electrical feedthrough prototypes.

Figure 9:
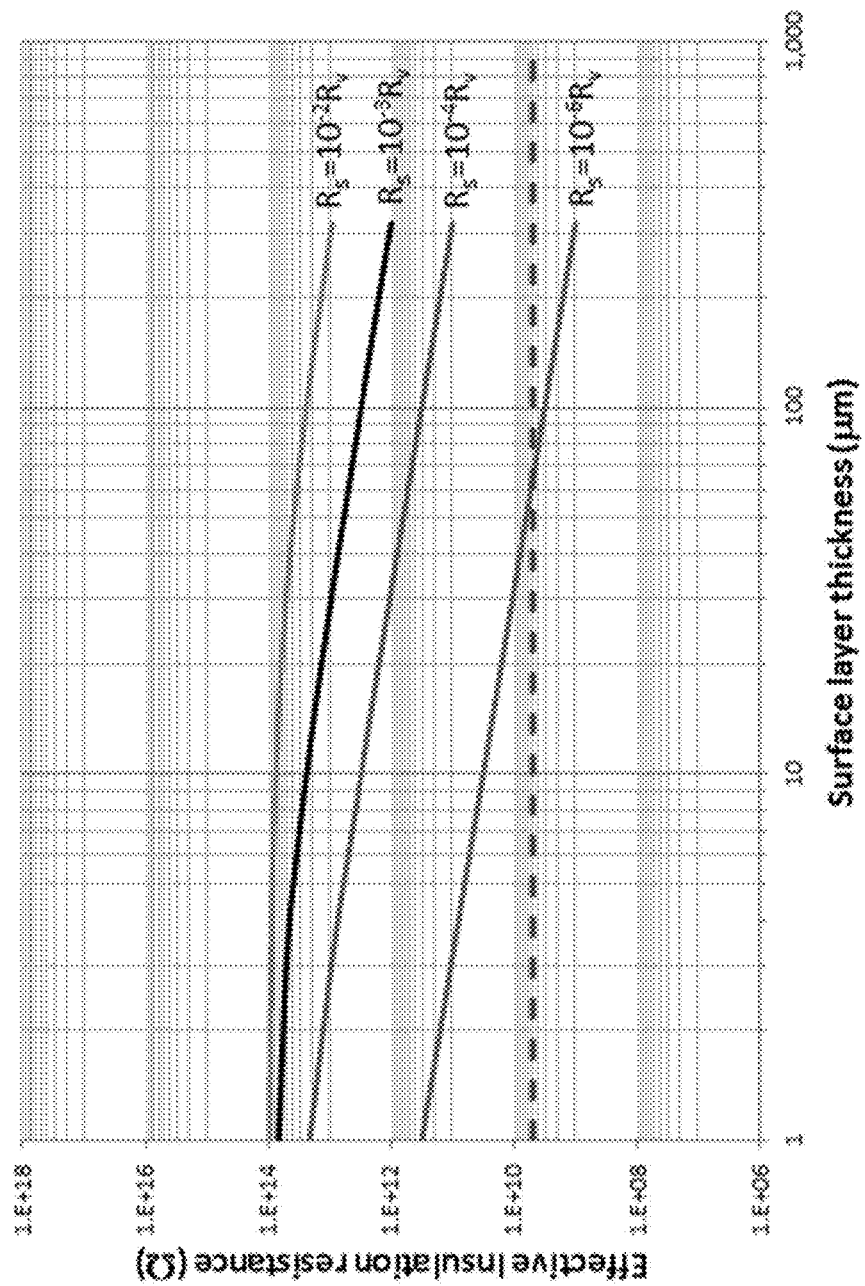
FIG. 9 shows a graph illustrating how the effective insulation resistance (IR) of example dielectric sealing material sealed electrical feedthrough packages could be significantly reduced if the thickness of the surface conductive layer is not negligible.

FIG. 9 shows a graph illustrating how the effective insulation resistance (IR) of example dielectric material sealed electrical feedthrough packages could be significantly reduced if the thickness of the surface water contained conductive layer with non negligible thickness. At the thickness of surface conductive layer is close to zero, the effective IR value should be around volumetric resistance of $R_v \approx 100$ TΩ, as used in FIG. 9. If surface resistance $R_s$ is lower than volumetric resistance $R_v$, the effective IR could be affected with increased surface layer thickness. However, water-contaminated surface layer will become more conductive so that the effective IR could also be reduced significantly. As indicated by ×10$^{-6}$ reduction in surface layer resistance the effective IR can be dropped to GΩ range within 60 µm thickness. Such a surface effect may be a good explanation on the measured IR value in FIG. 7. It is clear that $OH^{-1}$ hydroxyl ions contained fluid may be condensed onto the sealing material surface or permeated into subsurface of the sealing material.

Furthermore, the system 100 is to test the reliability of a dielectric sealing material 111 surrounding a portion of a conducting pin 112 for use in high pressure high temperature (HPHT) electrical feedthrough package to determine if it has sufficient insulation resistance under downhole hydraulic pressure of 30,000 PSI conditions. That is to determine whether a specific dielectric sealing material 111 has moisture permeability. Obviously, high moisture resistance and negligible permeability of a dielectric sealing material 111 will provide better reliability for a downhole electrical feedthrough used in water-based or moisture-rich wellbores. A dielectric sealing material 111 may not chemically interact with extrinsic hydroxyl ions, but high hydraulic pressure may force moisture permeating into the dielectric sealing material 111 that also could effectively reduce electrical resistance by significant conductive surface layer formation. The surface electrical resistivity of a dielectric sealing material 111, such as a polymer, glass, glass-ceramic or ceramic, could be remarkably lower than volume resistance, and the effective insulation resistance could become much smaller than the ambient IR value regardless of whether a dielectric sealing material 111 is of hydrophobicity. This is not due to chemical interaction between hydroxyl ions and the dielectric sealing material 111 but due to the moisture permeability in the dielectric sealing material 111. The moisture permeability of the dielectric sealing material 111 generally depends upon the density, nano-crystalline grain structure, morphology, and also upon the cooling rate of the electrical feedthrough after a hot manufacturing process.

An insulation resistance measurement unit 130 may be configured to measure the electrical resistance of a dielectric sealing material 111 that is surrounding a portion of a conducting pin 112 which are in a testing apparatus 150 via a first 113 and a second 114 electrical lead. Preferably, the first electrical lead 113 may be coupled to the conducting pin 112 and the second electrical lead 114 may be electrically coupled to the metal shell 153, where the dielectric sealing material 111 may be sandwiched between, or otherwise separate, the pin 112 and metal shell 153. In some embodiments, a second electrical lead 114 may be electrically coupled to the dielectric sealing material 111 by being in contact with or otherwise coupled directly to the dielectric sealing material 111. In preferred embodiments, a second electrical lead 114 may be electrically coupled to the dielectric sealing material 111 via one or more intermediary conducting devices, such as a plate 116 (FIGS. 2-5), so that electricity may freely flow between the second electrical lead 114 and the dielectric sealing material 111 via one or more intermediary conducting devices.

The first 113 and a second 114 electrical leads may each generally be an electrical connection, preferably comprising of a length of wire, such as copper, other low resistivity metal, or other electrically conducting material, which may be used to form an electric connection between two objects while allowing the two objects to be spaced remotely from each other. In preferred embodiments, the first 113 and a second 114 electrical leads may electrically couple an insulation resistance measurement unit 130 to a dielectric sealing material 111 and to a conducting pin 112 within a testing apparatus 150 thereby allowing the insulation resistance measurement unit 130 to measure insulation resistance between the dielectric sealing material 111 and conducting pin 112 by measuring an insulation resistance value between the electrical leads 113, 114, while allowing the insulation resistance measurement unit 130 to be positioned remotely from the apparatus 150.

In some embodiments, the system 100 may comprise a testing apparatus 150, a processor unit 131, a data logging unit 132, a temperature control unit 133, a pressure sensor 134, and/or a hydraulic pump 135. One or more of the components 150, 131, 132, 133, 134, and 135, may be communicatively coupled via a local interface 141. The local interface 141 can be, for example but not limited to, one or more buses or other wired or wireless connections, as is known in the art. The local mechanical and electrical interfaces 141 can have additional elements, which are omitted for simplicity, such as controllers, buffers (caches), drivers, repeaters, and receivers, among many others, to enable communications. Further, the local interface 141 may include address, control, and/or data connections to enable appropriate communications among the aforementioned components.

A processor unit 131 may have a processor hardware device for executing software instructions. The processor can be any custom made or commercially available processor, a central processing unit (CPU), an auxiliary processor among several processors, a semiconductor-based microprocessor (in the form of a microchip or chip set), or generally any device for executing software instructions. When in operation, the processor unit 131 may be configured to execute software stored within a memory, to communicate data to and from the one or more components 131, 132, 133, 134, and 135, and to generally control operations of one or more components 150, 131, 132, 133, 134, and 135, of the system 100 pursuant to the software instructions.

A data logging unit 132 may be used to store data. The data logging unit 132 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data logging unit 132 may incorporate electronic, magnetic, optical, and/or other types of storage media. In preferred embodiments, a data logging unit 132 may be used to record insulation resistance values of a dielectric sealing material 111 as well as time elapsed pressure and temperature data that a dielectric sealing material 111 is exposed to. In further embodiments, the processor unit 131 may retrieve data from the data logging unit 132 and determines the difference between a first sample insulation resistance (IR) value of a dielectric sealing material 111 at a first environmental condition, having a first temperature, a first pressure, and a first moisture content, and a second sample insulation resistance (IR) value of the dielectric sealing material 111 at a second environmental condition, having a second temperature, a second pressure, and a second moisture content, in which the difference is useful for determining moisture resistance of the dielectric sealing material 111.

A temperature control unit 133 may be used to control and manipulate the temperature of a dielectric sealing material 111 and conducting pin 112 and to record temperature data describing the temperature of a dielectric sealing material 111 and conducting pin 112. The temperature control unit 133 may be configured to maintain a dielectric sealing material 111 at one or more temperatures to form one or more environmental conditions. In preferred embodiments, the temperature control unit may heat a dielectric sealing material 111 and/or an electric feedthrough comprising a dielectric sealing material 111 to a temperature at least 177 degrees Celsius for simulating downhole nominal temperature and to 220 degrees Celsius for reliability tests. In some embodiments, a temperature control unit 133 may comprise a programmable furnace unit which may be used to subject a dielectric sealing material 111 and conducting pin 112 within the apparatus 150 to temperature environments for simulating downhole temperatures. In preferred embodiments, the temperature control unit 133 may comprise one or more thermocouples 142 which may be in thermal communication with the apparatus 150 and which may provide temperature data to the temperature control unit 133 and/or processor unit 131. In further embodiments, the processor unit 131 may receive temperature data from a thermocouple which may describe the temperature of a dielectric sealing material 111 and conducting pin 112 within the apparatus 150, and the processor unit 131 may provide the data to the data logging unit 132 and/or operate the temperature control unit 133 to subject the dielectric sealing material 111 and conducting pin 112 to one or more programmed temperatures. In preferred embodiments, a temperature control unit 133 may heat a dielectric sealing material 111 within the apparatus 150 to a temperature greater than 50 degrees Celsius, up to and including 300 degrees Celsius.

In some embodiments, the system 100 may comprise one or more hydraulic pumps 135 which may be used to pump testing or pressurizing fluid 115 into the testing chamber 151 of a testing apparatus 150 via a hydraulic line 143 coupled to a fluid conducting aperture 152. In preferred embodiments, a hydraulic pump 135 may be used to pump testing or pressurizing fluid 115 into the testing chamber 151 of a testing apparatus 150 to generate a pressure greater than 5,000 PSI up to and including 50,000 PSI. In further preferred embodiments, a hydraulic pump 135 may introduce a fluid 115 into the testing chamber 151 to generate a pressure greater than 2,000 PSI initially, and, preferably steadily, ramping up to one or more other pressures, such as 5,000 PSI, 10,000 PSI, 15,000 PSI, 20,000 PSI, 30,000 PSI and 35,000 PSI. A hydraulic pump 135 may comprise a pressurizing pump such as a gear pump, rotary vane pump, screw pump, bent axis pump, inline axial piston pumps and swashplate principle pumps, radial piston pumps, peristaltic pumps, or any other suitable type of fluid pressuring pump. A hydraulic line 143 may comprise any type of conduit or tubing suitable for conducting a fluid 115 at pressures generated by the hydraulic pump 135 up to and including 50,000 PSI.

In some embodiments, the system 100 may comprise one or more pressure sensors 134 which may be used to detect or determine the pressure of a fluid 115 provided to the testing chamber 151 and/or otherwise configured to measure the pressure within the testing chamber 151. Optionally, a pressure sensor 134 may be integral with a hydraulic pump 135 or otherwise coupled to a hydraulic line 143 or coupled with the testing chamber 151. A pressure sensor 134 may include silicon MEMS strain gauge sensors; pressure sensor piezoresistive silicon pressure sensors; analog output pressure transducer sensors; remote wireless pressure transducers; harsh media pressure sensors; digital output absolute pressure sensors; IsoSensor type pressure sensors; solid state pressure sensors; or any other type of pressure sensing method or device.

The system 100 may be configured to subject a dielectric sealing material 111 and conducting pin 112 within the apparatus 150 to a pressurized fluid to simulate down hole pressures. A dielectric sealing material 111 and a conducting pin 112 may be positioned within the apparatus 150 and exposed to the testing chamber 151 and a fluid 115 may be forced into contact with the dielectric sealing material 111 and conducting pin 112 by the hydraulic pump 135. In some embodiments, a fluid 115 may be a hydraulic pressurized fluid and comprise a heat transfer oil, such as Shell heat transfer oil S2 X, or other oil preferably with minimum film temperature of 310 degrees Celsius and minimum bulk temperature of 300 degrees Celsius, although other oils may be used. In other embodiments, a fluid 115 may be a hydraulic pressurized fluid and comprise de-ionized water useful for evaluating the impact of moisture on the dielectric sealing material 111. In still other embodiments, a fluid 115 may be a hydraulic pressurized fluid and comprise an aqueous solution useful for evaluating the impact of moisture on the dielectric sealing material 111. In alternative embodiments, a fluid 115 may be any hydraulic fluid capable of being pressurized by a hydraulic pump 135, and can be varied its moisture contents or relative humidity from 5-10% RH in one case, and 50-90% RH in the other case for example.

Figure 2:
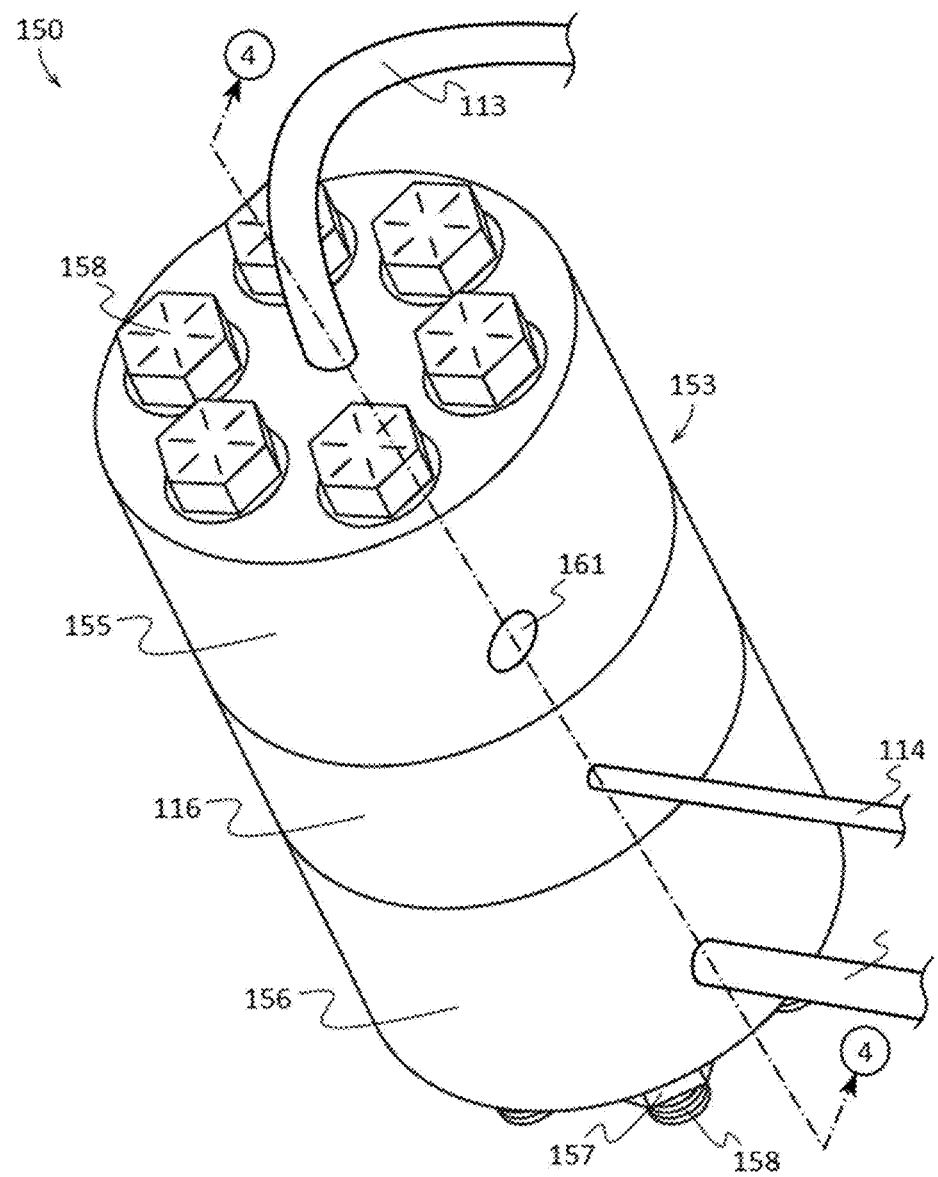
FIG. 2 illustrates a top perspective view of an example of a testing apparatus of a system for determining the impact of moisture on dielectric sealing materials according to various embodiments described herein.
Figure 3:
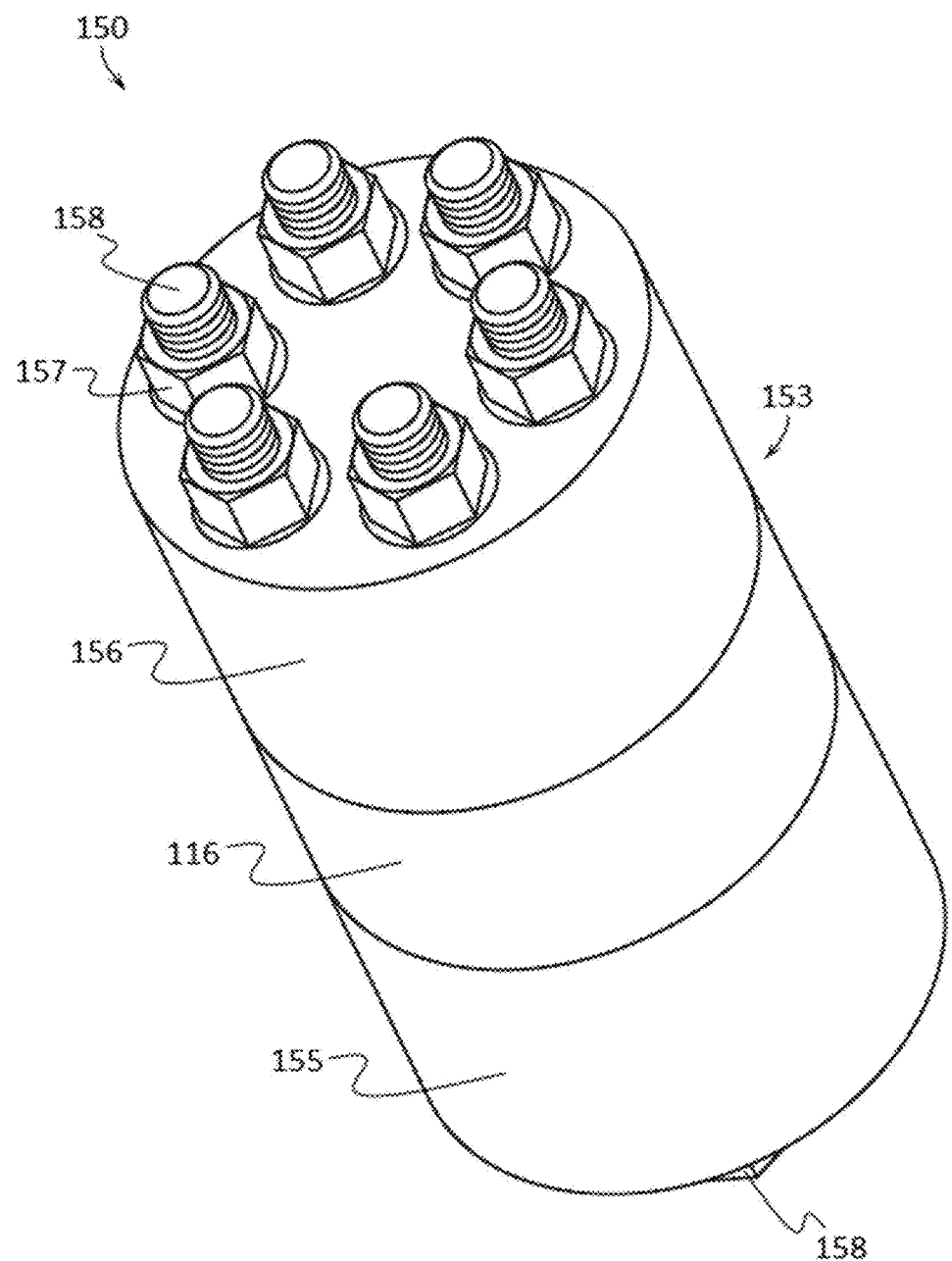
FIG. 3 shows a bottom perspective view of an example of a testing apparatus of a system for determining the impact of moisture on dielectric sealing materials according to various embodiments described herein.
Figure 4:
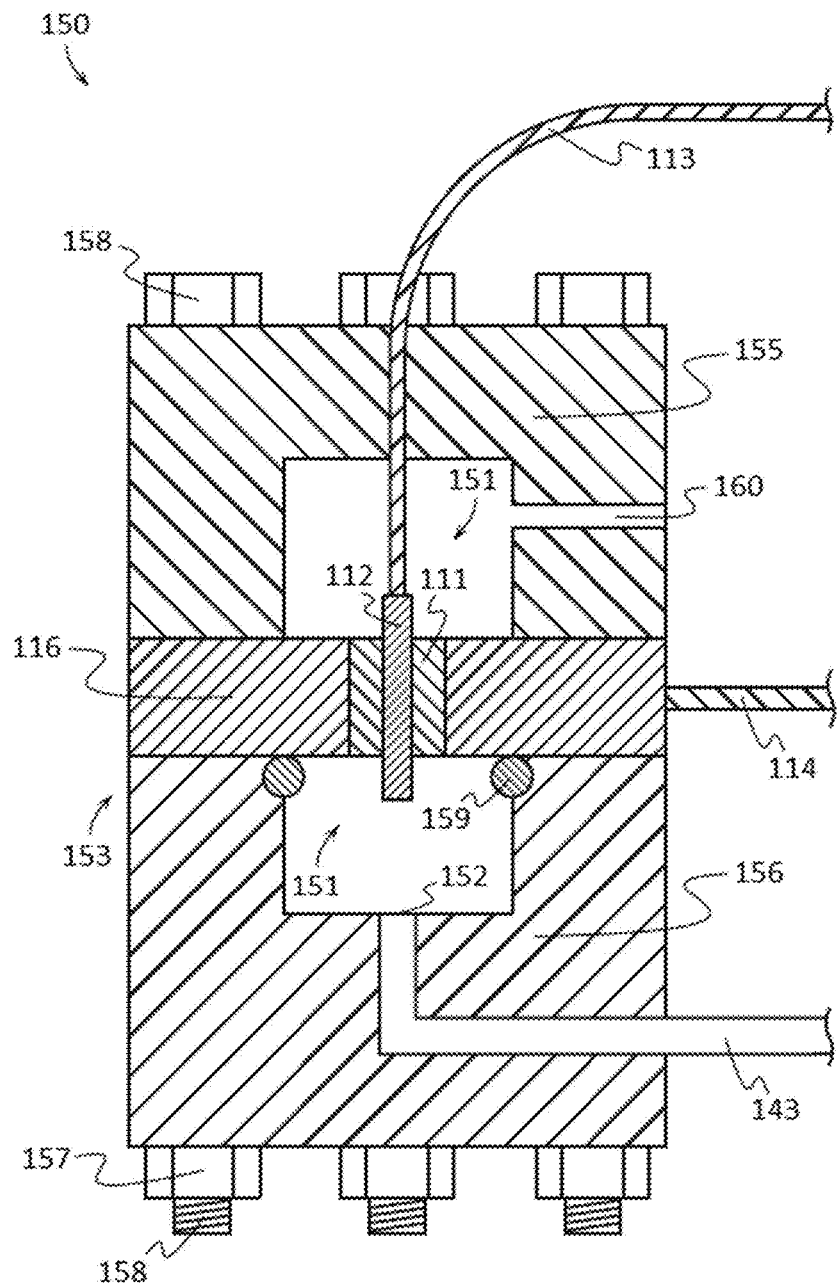
FIG. 4 depicts a sectional, through line 4-4 shown in FIG. 1, elevation view of an example of a testing apparatus of a system for determining the impact of moisture on dielectric sealing materials according to various embodiments described herein.
Figure 5:
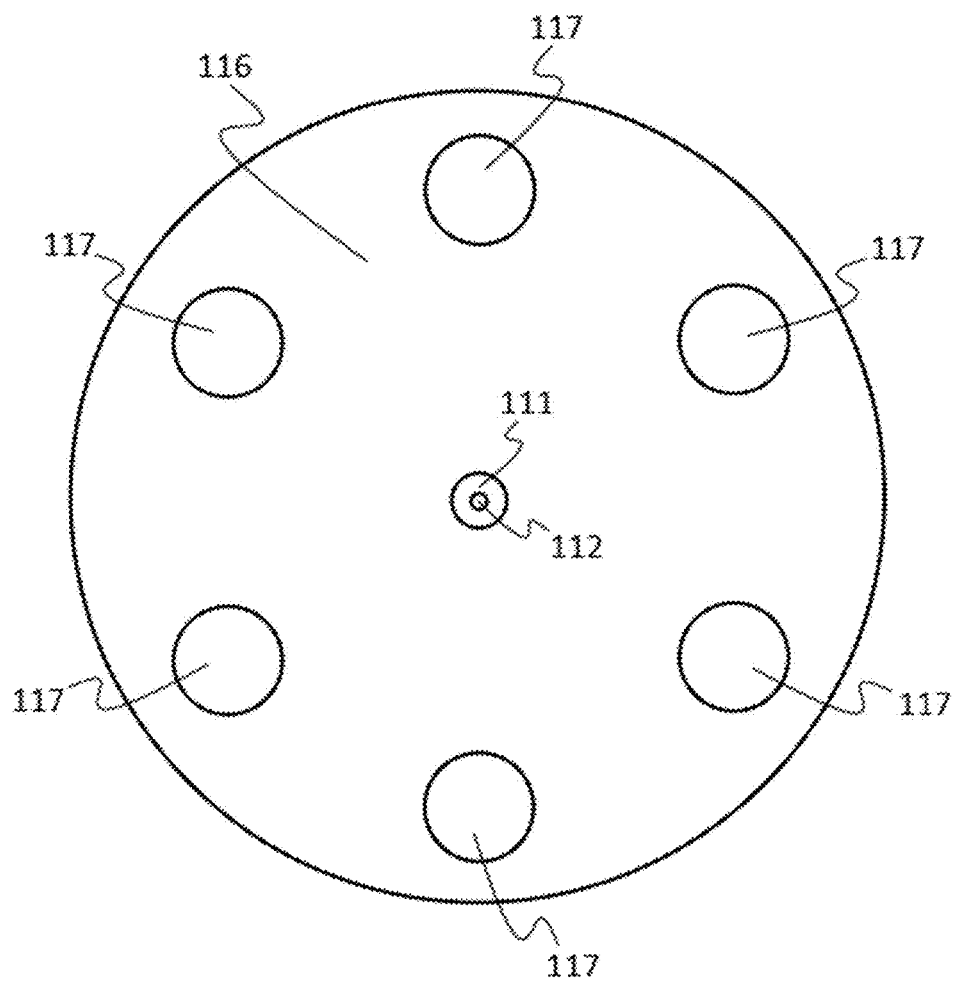
FIG. 5 illustrates a sectional, through line 5-5 shown in FIG. 1, elevation view of an example of a plate of a testing apparatus according to various embodiments described herein.

As perhaps best shown in FIGS. 2-4, the system 100 may comprise a testing apparatus 150 for determining the impact of moisture on dielectric materials. The apparatus 150 may be used to subject a dielectric sealing material 111, preferably in contact with a conducting pin 112, to elevated temperatures, to elevated pressures, and/or to a fluid 115 to simulate conditions which may be encountered in a bore hole. In some embodiments, the apparatus 150 may comprise a testing chamber 151 which may be surrounded by a rigid metal shell 153. A dielectric sealing material 111 may be positioned within the testing chamber 151, and the dielectric sealing material 111 may surround a conducting pin 112. A first electrical lead 113 may be coupled to the conducting pin 112, and a second electrical lead 114 may be electrically coupled to the dialectric sealing material 111. An insulation resistance measurement unit 130 may be coupled to both the first electrical lead 113 and the second electrical lead 114. The insulation resistance measurement unit 130 may be configured to measure an insulation resistance value between the electrical leads 113, 114. A fluid conducting aperture 152 may be positioned within the rigid metal shell 153, and the fluid conducting aperture 152 may be configured to transfer a fluid 115 into the testing chamber 151.

The apparatus 150 may comprise a metal shell 153 forming a testing chamber 151 suitable for withstanding elevated pressures and temperatures. A metal shell 153 may be made from or comprise a rigid material such as steel alloy 304L, AISI14041, Inconel alloy 718 or X750, and Titanium alloys, any other type of high strength material which may be substantially rigid for standing elevated temperatures, pressures, and contact with a hydraulic pressurized fluid 115. Preferably, the metal shell 153 may be made of or comprise an electrically conductive material. The metal shell 153 may be used to form a testing chamber 151 which may generally form a cavity and which may be used to expose a dielectric sealing material 111 and a conducting pin 112 to a hydraulic pressurized fluid 115 preferably at elevated temperatures.

In some embodiments, the metal shell 153 may comprise a fluid conducting aperture 152 in communication with the testing chamber 151. Preferably, a fluid conducting aperture 152 may enable a fluid 115 to enter the testing chamber 151 through a first flange 155 or a second flange 156. In further embodiments, the metal shell 153 may comprise an equilibrium aperture 161 in communication with the testing chamber 151. Preferably, an equilibrium aperture 161 may pass through a first flange 155 or a second flange 156 and may enable a portion of the testing chamber 151 to be in pressure equilibrium with the environment outside of the shell 153. Optionally, a first electrical lead 113 may pass through the metal shell via an equilibrium aperture 161 or by passing through the shell via any other suitable opening or method.

In some embodiments, the metal shell 153 may comprise two or more units which may be removably coupled together to form a testing chamber 151 and to enable a dielectric sealing material 111 and a conducting pin 112 to be positioned in and out of the testing chamber 151. In preferred embodiments, the metal shell 153 may comprise a first flange 155 and a second flange 156 which may be removably coupled together. In some embodiments, the first flange 155 may be removably coupled to the second flange 156 with one or more, such as a plurality, of nut 157 and bolt 158 fasteners. In other embodiments, the first flange 155 may be removably coupled to the second flange 156 with one or more, such as a plurality, of any other type of threaded fasteners, or any other suitable type of fastener. In alternative embodiments, the flanges 155, 156, may each comprise threading, and the first flange 155 may be removably coupled to the second flange 156 with the threading.

Optionally, the apparatus 150 may comprise a plate 116 which may be used to position a dielectric sealing material 111 and a conducting pin 112 within the apparatus 150 and exposed to the testing chamber 151. Preferably, a plate 116 may be made from a rigid material that is electrically conductive, such as steel alloys, AISI4041 and Inconel alloy 718 or X750. In some embodiments, a dielectric sealing material 111 may be welded or otherwise coupled to a plate 116 in an electrically conductive manner so that electrical resistance between the plate 116 and dielectric sealing material 111 may be negligible. In this manner, the plate 116 may serve as an electrical conductor between a second lead 114 and the dielectric sealing material 111. In further embodiments, a plate 116 may comprise one or more fastener apertures 117 which may be used to receive fasteners configured to couple a first flange 155 to a second flange 156, such bolt 158 fasteners, thereby allowing the flanges 155, 156, and plate 116 to be removably coupled together with the plate 116 positioned between the first flange 155 and the second flange 156.

In some embodiments, the apparatus 150 may comprise an o-ring 159 which may be positioned between the first flange 155 and the second flange 156. An o-ring 159 may function to seal the junction of two flanges 155, 156, to seal the junction between a first flange 155 and a plate 116, and/or to seal the junction between a second flange 156 and a plate 116 in order to prevent the leakage of fluid 115 from a junction. In some embodiments, an o-ring 159 may be or comprise a polymer material such as polyacrylate (ACM), ethylene acrylate (AEM), butyl rubber (IIR), polychloroprene rubber (CR), ethylene propylene rubber (EPM, EPR, EPDM), fluorosilicone (FVMQ), acrylontirile-butadiene (NBR), hydrogenated nitrile (HNBR, HSN), polyurethane (AU, EU), silicone rubber (VMQ, PVMQ), fluorocarbon (FKM, FPM), tetrafluoroethylene-propylene (AFLAS™), high performance fluoroelastomer (Hifluor™) perfluoroelastomer, and perfluoroelastomer (ULTRA). In other embodiments, an O-ring 159 may be replaced by a metal C-ring (such as from Parker Hannifin Corporation), which may be made from or comprise Alloy X750, Alloy 718, or any other suitable metal or metal alloy.

In preferred embodiments, the apparatus 150 may be in communication with a hydraulic pump 135 to allow the hydraulic pump 135 to communicate a fluid 115 into the testing chamber 151 through a fluid conducting aperture 152. Preferably, a dielectric sealing material 111 and a conducting pin 112 may be exposed in the test chamber 151 so that a pressurized fluid 115 may enter the fluid conducting aperture 152 to contact a first side of the dielectric sealing material 111. An optional plate 116 and the first side of the dielectric material 111 may prevent the fluid from exiting the testing chamber 151 and preferably from exiting the testing chamber 151 via an equilibrium aperture 161 that may be open to the atmosphere.

Figure 6:
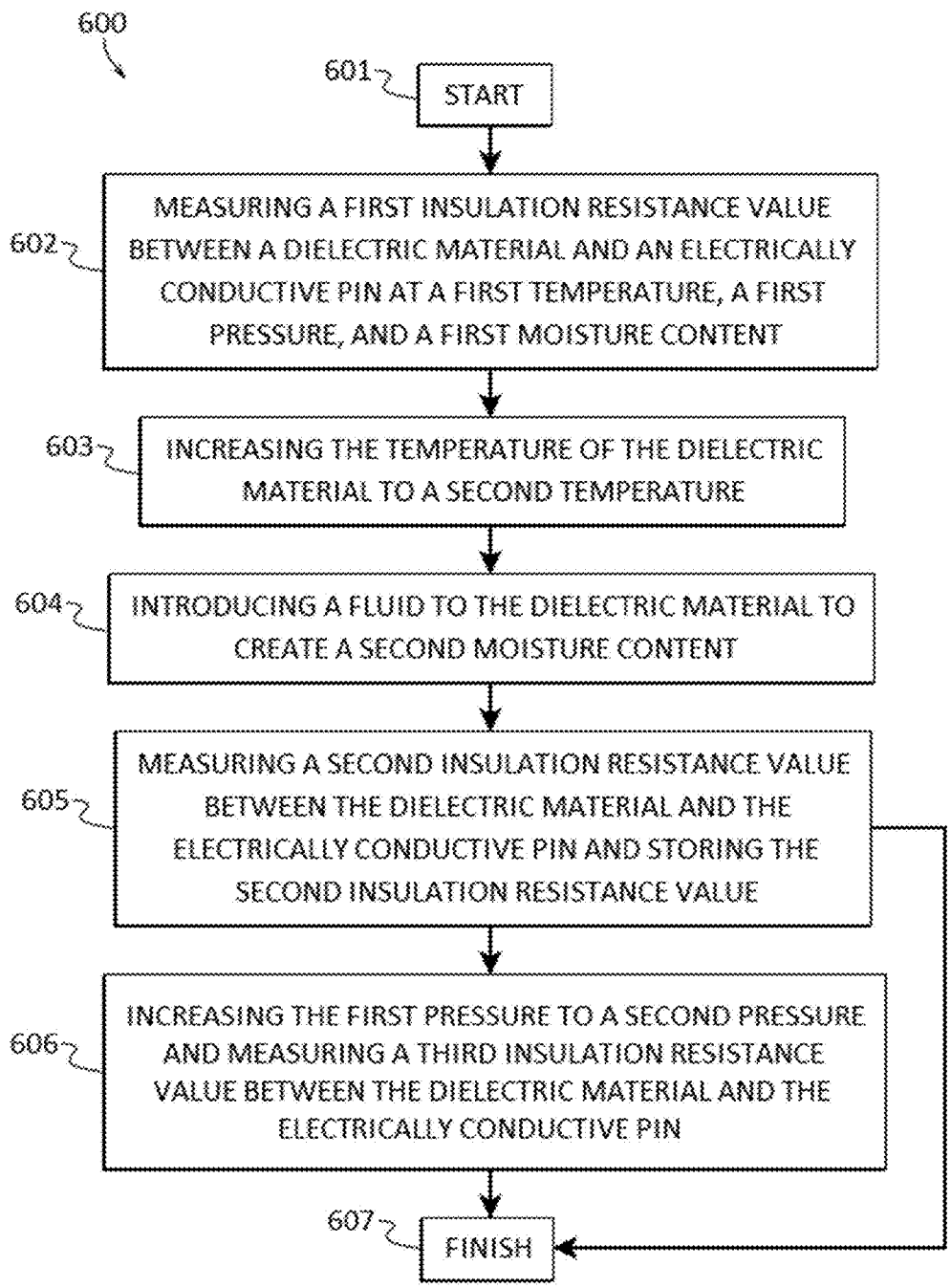
FIG. 6 shows a block diagram of an example of a method for determining the impact of moisture of a dielectric sealing material according to various embodiments described herein.

FIG. 6 shows a block diagram of an example of a method for determining the impact of moisture of a dielectric material ("the method") 600 according to various embodiments described herein. In some embodiments, the method 600 may determine the impact of moisture of a dielectric sealing material 111 which has a portion of a conducting pin 112 disposed within the dielectric sealing material 111 by determining the insulation resistance of the dielectric sealing material 111 at one or more conditions, such as the elevated temperature and pressure conditions which may occur in an open-hole.

In some embodiments, the method 600 may start 601 and a first insulation resistance value may be measured between the dielectric sealing material 111 and an electrically conductive pin 112 at a first temperature, a first pressure, and a first moisture content in step 602. The dielectric sealing material 111 and electrically conductive pin 112 may be positioned within a testing apparatus 120 and exposed to the testing chamber 151 at a first temperature, a first pressure, and a first moisture content. In some embodiments, the first temperature, first pressure, and first moisture content may be approximately ambient and/or room temperature conditions such as between 20 to 25 degrees Celsius, 1 atmosphere or approximately 14.70 PSI, and 30 to 50 percent humidity. In other embodiments, the first temperature, first pressure, and/or first moisture content may be any other value. In still further embodiments, the first moisture content may describe a lack of contact between the dielectric sealing material 111 and a fluid 115. In alternative embodiments, the first moisture content may describe a presence of contact between the dielectric sealing material 111 and a fluid 115. The first insulation resistance value may be measured by an insulation resistance measurement unit 130 having a first electrical lead 113 in electrical communication with, such as by being coupled to, the conducting pin 112 and a second lead 114 in electrical communication with, such as by being coupled to the metal shell 153 and/or plate 116 which may be coupled, the dielectric sealing material 111. Optionally, in step 602, the first insulation resistance value may be stored in a data logging unit 132.

In step 603, the temperature of the dielectric sealing material 111 may be changed to a second temperature that is different from the first temperature. In some embodiments, the testing apparatus 150 may be in thermal communication with a temperature control unit 133 and the temperature control unit 133 may change the temperature of the entire apparatus 150 to increasing the temperature of the dielectric sealing material 111 and testing chamber 151 to a second temperature. In alternative embodiments, a temperature control unit 133 may be in thermal communication with the dielectric sealing material 111 and testing chamber 151 with any other suitable method to enable the temperature of the dielectric sealing material 111 and testing chamber 151 to be increased or decreased from the first temperature to a second temperature. In preferred embodiments, the fluid 115 may be maintained at one or more second temperatures between 177 to 300 degrees Celsius for a time period or duration, such as one hour, three hours, ten hours, 25 hours, 200 hours, 500 hours, up to and including 1,000 hours. For example, the dielectric sealing material 111 and testing chamber 151 may be changed from a first temperature of 25 degrees Celsius to a second temperature of 177 degrees Celsius or from first temperature of 100 degrees Celsius to a second temperature of 220 degrees Celsius using a testing apparatus 150 with an O-ring seal or 300 degrees Celsius using a testing apparatus 150 with a metal C-ring seal.

In step 604, a fluid 115 may be introduced to the dielectric sealing material 111 to create a second moisture content that is different than the first moisture content. In some embodiments, a hydraulic pressurized or non-pressurized fluid 115 may be introduced to the dielectric sealing material 111 to create a second moisture content by placing the dielectric sealing material 111 into contact with the fluid 115 within a testing chamber 151. In other embodiments, a fluid 115 may be introduced to the dielectric sealing material 111 to create a second moisture content by allowing the fluid 115 to enter the testing chamber 151. In preferred embodiments, a hydraulic pump 135 may be used to introduce a fluid 115 to the dielectric sealing material 111 to create a second moisture content. In other embodiments, a testing apparatus 150 may be disassembled, the fluid 115 added to the testing chamber 151, and then the apparatus 150 assembled to introduce a fluid 115 to the dielectric sealing material 111 to create a second moisture content. In still other embodiments, a fluid 115 may be introduced to the dielectric sealing material 111 to create a second moisture content with any other suitable method.

In step 605, a second insulation resistance value may be measured between the dielectric sealing material 111 and the electrically conductive pin 112. Optionally, the dielectric sealing material 111 may be removed from the testing chamber 151 prior to measuring a second insulation resistance value. The second insulation resistance value may be measured by an insulation resistance measurement unit 130 having a first electrical lead 113 in electrical communication with the conducting pin 112 and a second lead 114 in electrical communication with the dielectric sealing material 111. For oil-based hydraulic pressurized soaking treatment, the IR can be directly measured without removing oil from the dielectric sealing material surface. However, before one is to measure boiling water soaking treated feedthrough prototypes the surface water fluid has to be puffed out to avoid electric arc from high voltage (500-2500 DCV) IR testing. Optionally, in step 605, the second insulation resistance value may be stored in a data logging unit 132. In some embodiments, the method 600 may include comparing the time elapsed IR value with ambient first measured values; fitting or comparing the measured time elapsed IR values to a power response function as an indication of acceptable moisture resistance for a dielectric sealing material used for downhole electrical feedthrough package; and fitting or comparing the measured time elapsed IR values to a negative exponential function of elapsed time as an indication a dielectric sealing material is not appropriate used for downhole electrical feedthrough package.

Optionally, the method 600 may comprise step 606 of increasing the first pressure to a second pressure different from the first pressure and measuring a third insulation resistance value between the dielectric sealing material 111 and the electrically conductive pin 112 with the insulation resistance measurement unit 130. In some embodiments, the first pressure may be increased to a second pressure through a hydraulic pump 135 acting on the fluid 115 which may force the fluid 115 into the testing chamber 151 via a fluid conducting aperture 152 to which the hydraulic pump 135 is in fluid communication with. In preferred embodiments, the fluid 115 may be maintained at a second pressure of 2,000 PSI to 35,000 PSI for a time period or duration, such as one hour, three hours, ten hours, 25 hours, 200 hours, 500 hours, up to and including 1,000 hours. In further preferred embodiments, steps 603 and 606 may be concurrent so that the fluid 115 may be maintained at one or more second temperatures between 177 to 300 degrees Celsius for a time period or duration and maintained at a second pressure of 2,000 PSI to 35,000 PSI for a time period or duration, such as one hour, three hours, ten hours, 25 hours, 200 hours, 500 hours, up to and including 1,000 hours and then an insulation resistance value may be measured between the dielectric sealing material 111 and the electrically conductive pin 112. Optionally, in step 606, the third insulation resistance value may be stored in a data logging unit 132.

After step 605 or optional step 606, the method 600 may finish 607.

Figure 10:
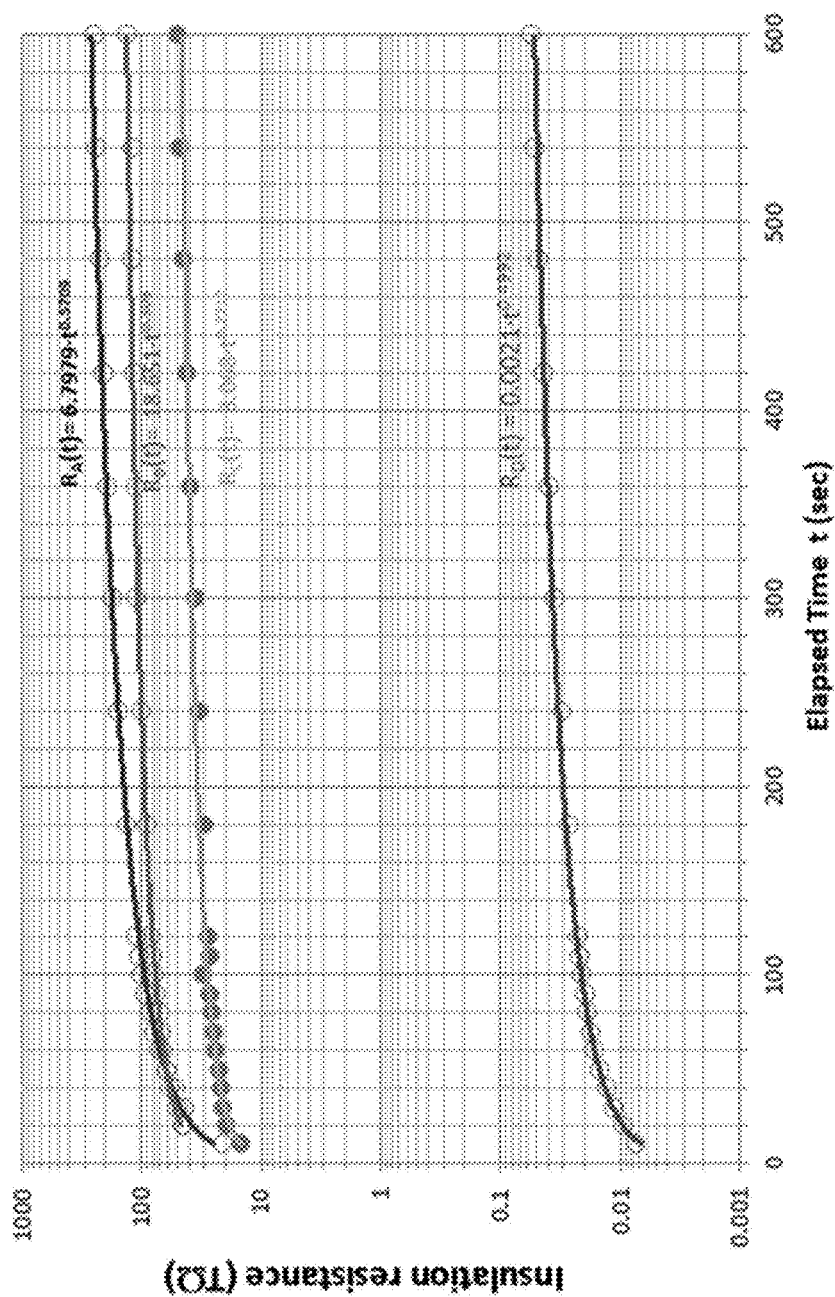
FIG. 10 depicts a graph showing the measured effective insulation resistance data from four example dielectric sealing materials after 24 hours 30,000 PSI hydraulic pressurized water soaking process.

Additionally, the method 600, system 100, and/or apparatus 150 may be used for identifying if a dielectric sealing material 111 has moisture permeability, which may be based on a water-based hydraulic pressurized test. In some embodiments, a high moisture-resistant dielectric sealing material may be characterized by a power response function of $R(t)=R_o \cdot t^v$, while moisture sensitive dielectric sealing material may be characterized by a negative exponential function of $R(t)=R_o \cdot \exp(-at)$. In further embodiments, the initial test of the method 600 may be under hydraulic pressurized water soaking for at least 1 hour at ambient or room temperature. FIG. 10 provides an example of the measured effective insulation resistance data from four dielectric sealing materials 111 (A, B, C, and D) after 24 hours at 30,000 PSI hydraulic pressurized water soaking process. First, all four sealing materials have also shown positive response as a power function of time, namely, $R(t)=R_o t^v$ (v is constant). First three sealing materials have their insulation resistance values of 50-200 TΩ, while fourth sealing material has shown about 50 GΩ IR value. By comparing with ambient dry IR values of 50 TΩ to a few hundred TΩ the first three insulation resistance data from four dielectric sealing materials 111 (A, B, C, and D) after 24 hours 30,000 PSI hydraulic pressurized water soaking process treatment. First, all four dielectric sealing materials 111 have also shown positive response as a power function of time, namely, $R(t)=R_o t^v$ (v is constant). It is worth pointing out that, by referring FIG. 10 that, first three dielectric sealing materials 111 have their insulation resistance values of 50-200 TΩ, while fourth dielectric sealing material 111 has shown about 50 GΩ IR value after such a water-based 30,000 PSI hydraulic pressurized soaking process treatment. By comparing with ambient dry IR values of 50 TΩ to a few hundred TΩ the first three dielectric sealing materials 111 may be of better insulation strength for being used as HPHT downhole electrical feedthrough dielectric sealing materials. However, the fourth dielectric sealing materials 111 based electrical feedthrough may be not an adequate or suitable candidate for water-based wellbore or moisture-rich wellbore deployment, since the significant reduced IR value in dielectric sealing material D may strongly imply a significantly conductive surface layer formation or potential micro cracking in the sealing material, after water-based hydraulic pressurized water soaking process treatment.

Figure 11:
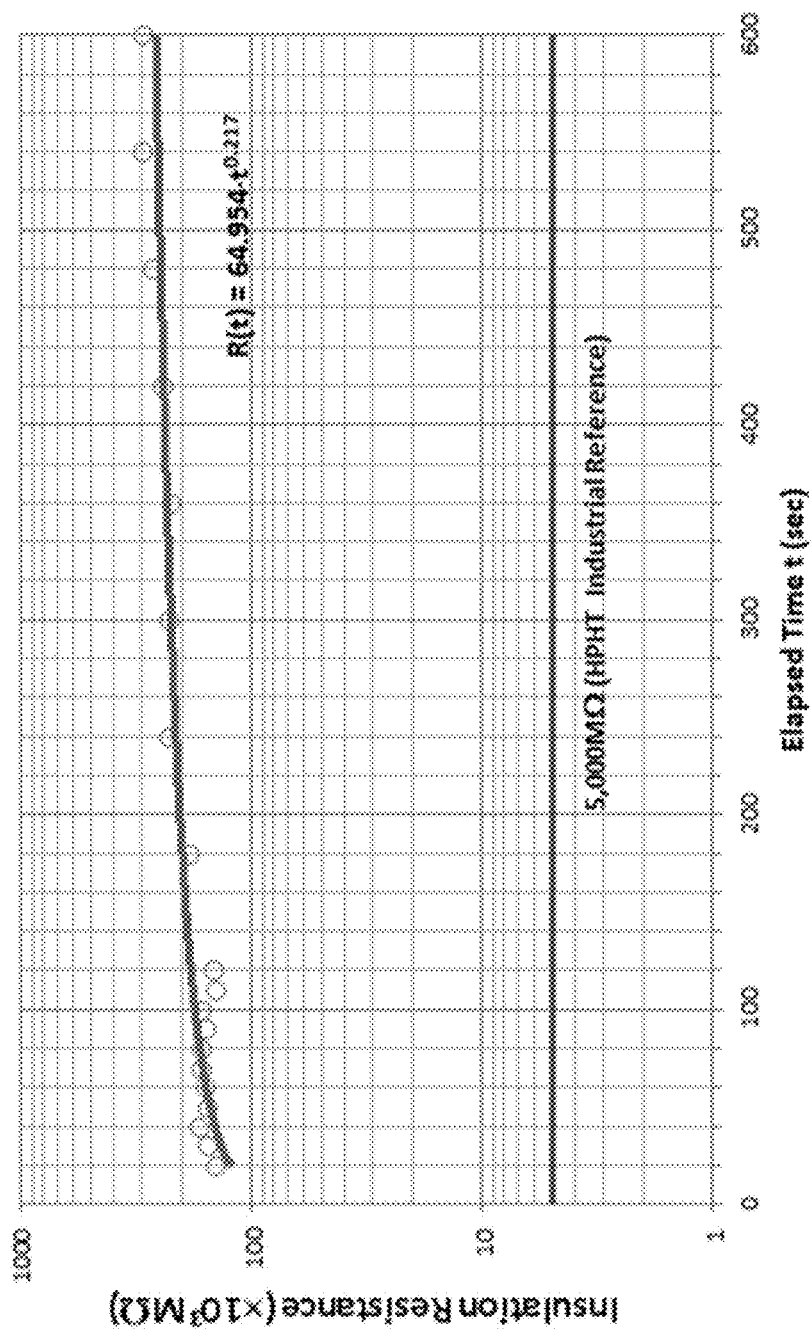
FIG. 11 illustrates a graph showing the measured effective insulation resistance under 7 hour, water-based 25 ksi and 200° C. hydraulic pressurized water soaking process on an example dielectric sealing material.

FIG. 11 illustrates a graph showing the measured effective insulation resistance under 7 hour, water-based 25 ksi and 200° C. hydraulic pressurized water soaking process on an example dielectric sealing material A, where both temperature and hydraulic pressurization have demonstrated the formation of conductive layer, potential by white-colored scaling process from testing system fluid system or an chemical interaction between the dielectric sealing material and high pressurized water under elevated temperature. Nevertheless, the measured effective IR value still shows a power function of the time, with averaged IR value around (200±50) GΩ, which is about 40 times higher than 5,000

MΩ, a nominal baseline reference used in HPHT industrial standard. If the less insulating surface layer resistance is reduced from original 100 TΩ to about 500 GΩ, the corresponding moisture affected layer thickness may be possible close to 100 μm, as estimated by FIG. 9. However, this measured IR value could be acceptable if this IR drop will keep >5,000 MΩ even having a surface layer of scaling or fouling contaminations.

While some materials have been provided, in other embodiments, the elements that comprise the apparatus 150 such as the shell 153, first flange 155, second flange 156, optional plate 116, and/or any other element discussed herein may be made from durable materials such as aluminum, steel, other metals and metal alloys, wood, hard rubbers, hard plastics, fiber reinforced plastics, carbon fiber, fiber glass, resins, polymers or any other suitable materials including combinations of materials. In some embodiments, one or more of the elements that comprise the apparatus 150 may be coupled or connected together with heat bonding, chemical bonding, adhesives, clasp type fasteners, clip type fasteners, rivet type fasteners, threaded type fasteners, ratchet type fasteners, a push-to-lock type connection method, a turn-to-lock type connection method, slide-to-lock type connection method or any other suitable temporary connection method as one reasonably skilled in the art could envision to serve the same function. In further embodiments, one or more of the elements that comprise the apparatus 150 may be coupled by being one of connected to and integrally formed with another element of the apparatus 150.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A system for determining the impact of moisture on a dielectric sealing material, the system comprising:
    a testing apparatus comprising a testing chamber, the testing chamber surrounded by a rigid shell;
    a dielectric sealing material and a conducting pin positioned within the rigid shell and exposed to the testing chamber;
    a first electrical lead coupled to the conducting pin;
    a second electrical lead coupled to the testing apparatus, the dialectic sealing material positioned between the first electrical lead and the second electrical lead;
    an insulation resistance measurement unit coupled to both the first electrical lead and the second electrical lead, the insulation resistance measurement unit configured to measure an insulation resistance value between the electrical leads;
    a fluid conducting aperture positioned within the rigid shell, the fluid conducting aperture configured to transfer a fluid into the testing chamber; and
    wherein the insulation resistance measurement unit measures a first insulation resistance value of the dielectric sealing material in a first environmental condition, and the insulation resistance measurement unit measures a second insulation resistance value of the dielectric sealing material at a second environmental condition after a hydraulic pressurized fluid has been introduced into the testing chamber.

2. The system of claim 1, wherein the rigid metal shell comprises a first flange and a second flange.

3. The system of claim 2, wherein the first flange is removably coupled to the second flange with a plurality of bolt fasteners, and wherein a plate holding the dielectric material is positioned between the first flange and the second flange.

4. The system of claim 3, wherein an O-ring is positioned between the first flange and the second flange to seal the hydraulic pressurized fluid inside the testing chamber.

5. The system of claim 1, wherein the hydraulic pressurized fluid is a hydraulic pressurized fluid comprising a heat transfer oil with minimum film temperature of 310 degrees Celsius and minimum bulk temperature of 300 degrees Celsius.

6. The system of claim 1, wherein the fluid is a hydraulic pressurized fluid comprising de-ionized water useful for evaluating the impact of moisture on the dielectric sealing material performance by simulating water-based or moisture-rich downhole conditions.

7. The system of claim 1, further comprising a hydraulic pump, the hydraulic pump configured to communicate the fluid into the testing chamber through the fluid conducting aperture.

8. The system of claim 7, wherein the hydraulic pump introduces the fluid into the chamber to generate a pressure greater than 2,000 PSI.

9. The system of claim 7, further comprising a pressure sensor configured to measure the pressure within the testing chamber.

10. The system of claim 1, further comprising a temperature control unit, the temperature control unit configured to maintain the dielectric sealing material at elevated temperatures in the second environmental condition.

11. The system of claim 10, wherein the temperature control unit heats the dielectric material to a temperature greater than 50 degrees Celsius.

12. The system of claim 1, further comprising a data logging unit to record the first insulation resistance value and the second insulation resistance value, as well as time elapsed pressure and temperature data.

13. The system of claim 12, wherein a processor unit retrieves data from the data logging unit and determines the difference between the first sample IR value and the second sample IR value, the difference useful for determining moisture resistance of the dielectric sealing material.

14. A testing apparatus for determining the impact of moisture on a dielectric sealing material, the apparatus comprising:
    a testing chamber surrounded by a rigid shell;
    a dielectric sealing material positioned within the testing chamber, the dielectric sealing material surrounding a conducting pin;
    a first electrical lead coupled to the conducting pin;
    a second electrical lead electrically coupled to the dialectic material;
    an insulation resistance measurement unit coupled to both the first electrical lead and the second electrical lead, the insulation resistance measurement unit configured to measure an insulation resistance value between the electrical leads; and
    a fluid conducting aperture positioned within the rigid shell, the fluid conducting aperture configured to transfer a fluid into the testing chamber.

15. The apparatus of claim 14, in communication with a hydraulic pump, the hydraulic pump configured to communicate the fluid into the testing chamber through the fluid conducting aperture.

16. The apparatus of claim 14, further comprising a plate, the plate holding the dielectric sealing material in a position exposing the dielectric sealing material to the testing chamber.

17. A method for determining the impact of moisture of a dielectric sealing material, the method comprising:
   measuring a first insulation resistance value between the dielectric material and an electrically conductive pin at a first temperature, a first pressure, and a first moisture content and storing the first insulation resistance value in a data logging unit;
   introducing a fluid to the dielectric sealing material to create a second moisture content and increasing the temperature of the dielectric sealing material to a second temperature; and
   measuring a second insulation resistance value between the dielectric sealing material and the electrically conductive pin and storing the second insulation resistance value in the data logging unit.

18. The method of claim 17, further comprising the step of increasing the first pressure to a second pressure through a pump acting on the fluid and measuring a third insulation resistance value between the dielectric material and the electrically conductive pin and storing the third insulation resistance value in the data logging unit.

19. The method of claim 17, wherein the fluid is a hydraulic pressurized fluid selected from one of: de-ionized water, a heat transfer oil, and a combination of both de-ionized water and heat transfer oil.

20. The method of claim 18 wherein the second temperature is greater than 50 degrees Celsius and the second pressure is greater than 5,000 PSI.

* * * * *